(12) United States Patent
Tsukerman et al.

(10) Patent No.: US 9,655,574 B2
(45) Date of Patent: May 23, 2017

(54) METHODS AND SYSTEMS FOR CONTROLLING MOVEMENT OF DETECTORS HAVING MULTIPLE DETECTOR HEADS

(71) Applicant: General Electric Company, Schenectady, NY (US)

(72) Inventors: Leonid Tsukerman, Q. Mozkin (IL); Jean-Paul Bouhnik, Tirat Carmel (IL); Yaron Hefetz, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/837,837

(22) Filed: Aug. 27, 2015

(65) Prior Publication Data

US 2015/0359496 A1    Dec. 17, 2015

Related U.S. Application Data

(63) Continuation of application No. 14/016,939, filed on Sep. 3, 2013, now Pat. No. 9,144,411.

(51) Int. Cl.
| | | |
|---|---|---|
| *A61B 6/00* | (2006.01) | |
| *A61B 6/10* | (2006.01) | |
| *A61B 6/03* | (2006.01) | |
| *A61B 6/04* | (2006.01) | |

(52) U.S. Cl.
CPC .......... *A61B 6/4452* (2013.01); *A61B 6/0407* (2013.01); *A61B 6/102* (2013.01); *A61B 6/4266* (2013.01); *A61B 6/4447* (2013.01); *A61B 6/5205* (2013.01); *A61B 6/037* (2013.01); *A61B 6/0414* (2013.01)

(58) Field of Classification Search
CPC ........ A61B 5/05; A61B 6/4447; A61B 6/5205
See application file for complete search history.

(56) References Cited

U.S. PATENT DOCUMENTS

| | | | |
|---|---|---|---|
| 4,149,079 A | 4/1979 | Ben-Zeev et al. | |
| 5,367,169 A | 11/1994 | Pierfitte | |
| 5,534,701 A | 7/1996 | Pierfitte et al. | |
| 5,838,009 A | 11/1998 | Plummer et al. | |
| 6,137,109 A | 10/2000 | Hayes | |
| 6,272,368 B1 * | 8/2001 | Alexandrescu | .......... A61B 6/08 250/349 |

* cited by examiner

*Primary Examiner* — Peter Luong
(74) *Attorney, Agent, or Firm* — Dean D Small; The Small Patent Law Group, LLC

(57) ABSTRACT

Methods and systems for controlling movement of detectors having multiple detector heads are provided. One system includes a gantry, a patient support structure supporting a patient table thereon, and a plurality of detector units. At least some of the detector units are rotatable to position the detector units at different angles relative to the patient table. The imaging system further includes a detector position controller configured to control the position of the rotatable detector units, wherein at least some of the rotatable detector units positioned adjacent to each other have an angle of rotation to allow movement of the rotatable detector units a distance greater than a gap between adjacent rotatable detector units. The detector position controller is configured to calculate at least one of field of view avoidance information or collision avoidance information to determine an amount of movement for one or more of the rotatable detector units.

18 Claims, 6 Drawing Sheets

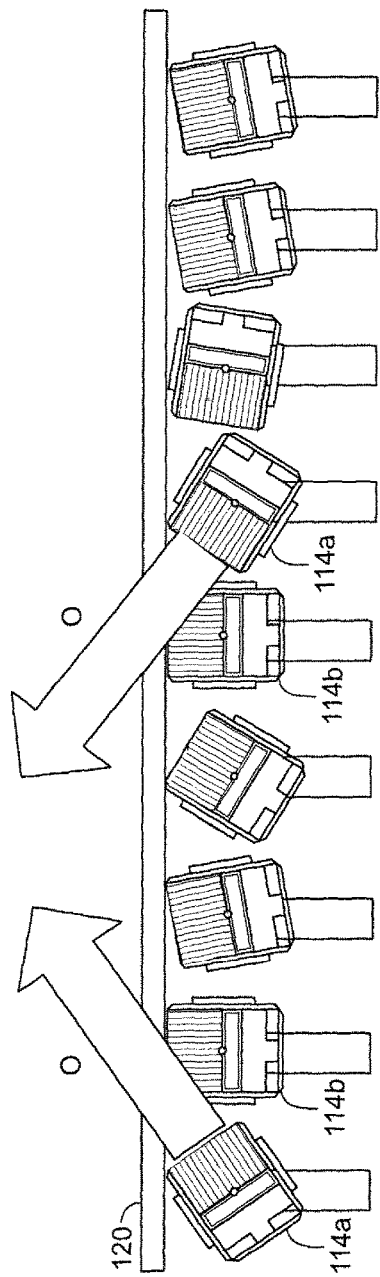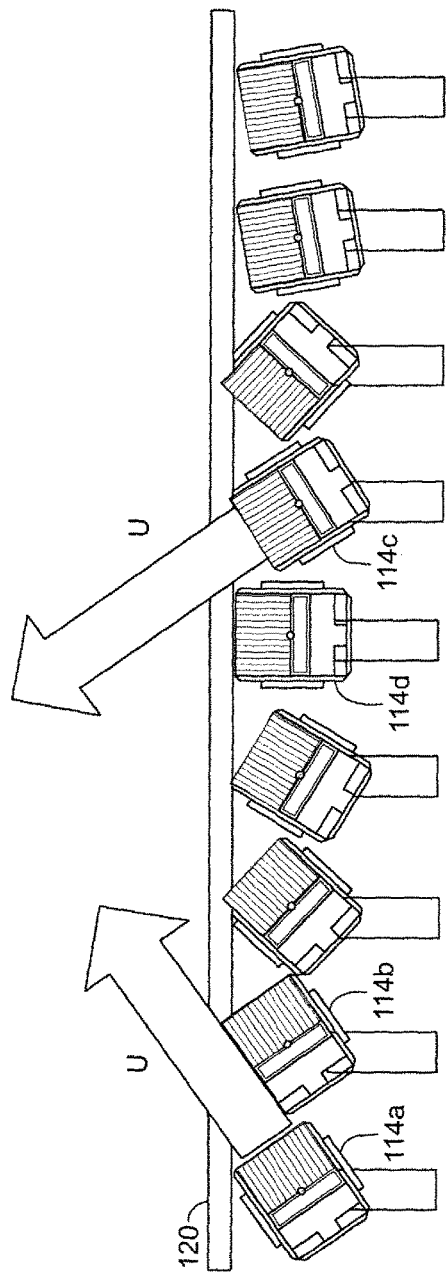

METHODS AND SYSTEMS FOR CONTROLLING MOVEMENT OF DETECTORS HAVING MULTIPLE DETECTOR HEADS

CROSS-REFERENCE TO RELATED APPLICATIONS

This application is a continuation application of, and claims benefit to the filing date of, U.S. patent application Ser. No. 14/016,939, filed Sep. 3, 2013, entitled "Methods and Systems for Controlling Movement of Detectors Having Multiple Detector Heads", the entire disclosure of which is incorporated by reference herein.

BACKGROUND OF THE INVENTION

The subject matter disclosed herein relates generally to systems and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data. However, in some instances when the orientation and movement of the detector heads is changed, one or more detector heads may obstruct the view of other detector heads.

Additionally, in NM imaging systems, the resolution of the detector, such as a gamma detector, is determined by the resolution of the detector (based on the size of pixels of the detector) and the resolution of a collimator attached to the detector. The resolution degrades with distance of the detector, specifically the collimator, from the subject.

In Single Photon Emission Computed Tomography (SPECT) systems having moving detector heads, the detectors may be positioned to focus on a region of interest. However, because of the size and spacing of the detector heads, when imaging a smaller subject (e.g., pediatric scan), the detector heads may collide when moved in close proximity to the subject, thereby preventing placement of the detector heads close to the subject. Moreover, for larger subjects, gaps may exist between the detectors because the detectors have to be moved apart to allow for focusing on the field of view, which can result in reduced sensitivity. Additionally, for odd shaped subjects or positions, such as where hands are placed to the side of a torso, in order to avoid collisions of the detector heads, the distribution of heads may not be optimal.

Accordingly, because the detector heads cannot be moved in close proximity to the subject, or as a result of other detector head placement difficulties or gaps between the detector heads, image resolution or sensitivity is reduced.

BRIEF DESCRIPTION OF THE INVENTION

In one embodiment, an imaging system is provided that includes a gantry, a patient support structure supporting a patient table thereon, and a plurality of detector units coupled to at least one of the gantry or the patient support structure. The plurality of detector units are arranged in an array, wherein at least some of the detector units are rotatable to position the detector units at different angles relative to the patient table. The imaging system further includes a detector position controller configured to control the position of the rotatable detector units, wherein at least some of the rotatable detector units are positioned adjacent to each other and have an angle of rotation to allow movement of the rotatable detector units a distance greater than a gap between adjacent rotatable detector units The detector position controller is further configured to calculate at least one of field of view avoidance information or collision avoidance information to determine an amount of movement for one or more of the rotatable detector units.

In another embodiment, a Nuclear Medicine (NM) imaging system is provided that includes a gantry, a patient support structure supporting a patient table thereon, a support member coupled to the gantry, and a plurality of movable detector carriers coupled to the support member and to the patient support structure, wherein each of the plurality of movable detector carriers has a distal end. The NM imaging system further includes at least one rotatable detector unit coupled to each of the distal ends of the plurality of movable detector carriers, wherein the rotatable detector units are rotatable about the distal end of the movable detector carrier to acquire NM image data. The NM imaging system also include a detector position controller configured to control the position of the rotatable detector units, wherein at least some of the rotatable detector units are positioned adjacent to each other and have an angle of rotation to allow movement of the rotatable detector units a distance greater than a gap between adjacent rotatable detector units. The detector position controller is further configured to calculate at least one of field of view avoidance information or collision avoidance information to determine an amount of movement for one or more of the rotatable detector units.

In another embodiment, a method for controlling movement of detector units is provided. The method includes determining at least one of position or a field of view information for a plurality of rotatable detector units and determining rotating movement of at least one of the rotatable detector units. The method further includes calculating at least one of field of view avoidance information or collision avoidance information corresponding to an amount of the determined rotating movement and generating one or more position adjustment signals based on the calculated field of view avoidance information or collision avoidance information. The method also includes controlling movement of the plurality of rotatable detector units using the one or more position adjustment signals.

BRIEF DESCRIPTION OF THE DRAWINGS

FIG. 3 is a schematic block diagram showing movement of detector units and illustrating field of view obstruction.

FIG. 4 is a schematic block diagram illustrating movement of detector units in accordance with various embodiments.

DETAILED DESCRIPTION OF THE INVENTION

Figure 1:
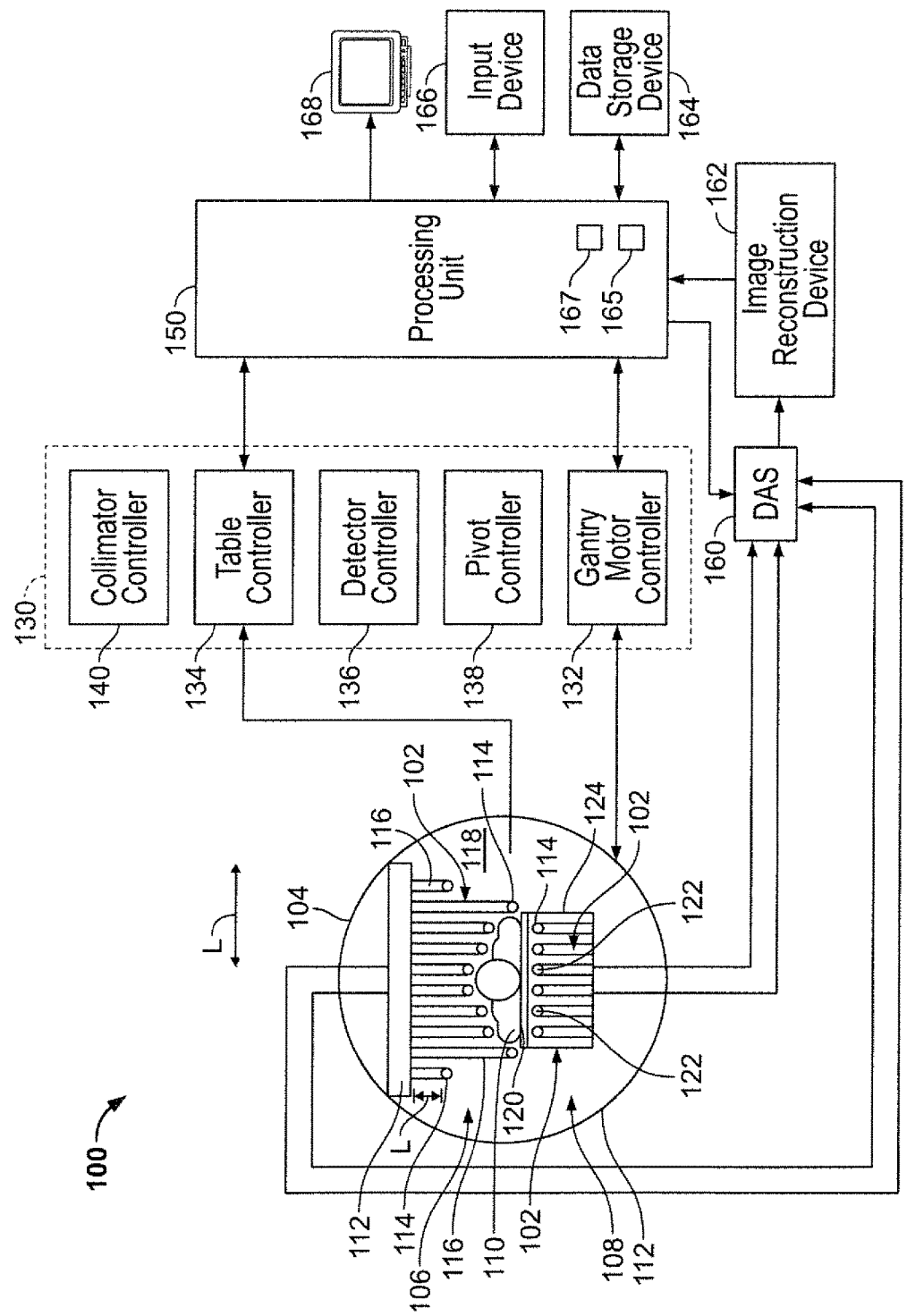
FIG. 1 is a schematic block diagram of a Nuclear Medicine (NM) imaging system in accordance with an embodiment.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide methods and systems for controlling the movement of a plurality of imaging detectors to position the imaging detectors to acquire image data. For example, in various embodiments a Nuclear Medicine (NM) imaging system with an array of detector heads that are individually and independently movable is provided. In some embodiments, one or more of the heads are capable of a plurality of types of movement, such as rotation and linear motion. For example, the detector heads may be configured to be positioned adjacent or proximate a subject and rotated, such as to increase the field of view of the detector heads. At least one technical effect of some embodiments is increased resolution or sensitivity of the NM imaging system. At least one technical effect of some embodiments is reduced likelihood that one detector head obstructs the field of view of another detector head. At least one technical effect of various embodiments is closer positioning or packing of a plurality of detector elements or heads, such as within an enclosure or a patient support.

FIG. 1 is a schematic illustration of a NM imaging system 100 having a plurality of imaging detectors mounted on a gantry. The movement of the imaging detectors is controlled to (i) reduce the likelihood or avoid collision among the moving imaging detectors and/or (ii) reduce the likelihood of one imaging detector obstructing the field of view of another imaging detector. For example, the NM imaging system in some embodiments provides coordinated swinging or rotating motion of a plurality of imaging detectors or detector heads.

In particular, a plurality of imaging detectors 102 are mounted to a gantry 104 and/or a patient support structure 124 (e.g., within the patient support structure 124 under a patient table 110), which may define a table support for a patient table 120. In the illustrated embodiment, the imaging detectors 102 are configured as two separate detector arrays 106 and 108 positioned above and below the subject 110 (e.g., a patient), as viewed in FIG. 1. The detector arrays 106 and 108 may be coupled directly to the gantry 104 and/or patient support structure 124, or may be coupled via support members 112 thereto, to allow movement of the entire arrays 106 and/or 108 relative to the gantry 104 (e.g., translating movement in the left or right direction as viewed in FIG. 1) or the patient support structure 124 (e.g., swinging or rotating movement under the patient 110). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104 or within the patient support structure 124. In some embodiments, the detector carriers 116 allow movement of the detector units 114 towards and away from the subject 110, such as linearly. Thus, in the illustrated embodiment the detector arrays 106 and 108 are mounted above and below the subject 110 and may allow linear movement of the detector units 114 (indicated by the arrow L), such as generally parallel to the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112, gantry 104, and/or patient support structure 124, which in various embodiments allows the detector units 114 to move linearly towards and away from the support member 112, such as radially inward and outwards for positioning adjacent the subject 110. For example, as described herein, the detector units 114 may be controlled to move independently of each other towards or away from the patient 110, as well as capable or rotational, pivoting, or tilting movement in some embodiments.

Each of the imaging detectors 102 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 110 may be formed with an aperture 118 (e.g., opening or bore) therethrough as illustrated. The patient table 120 is configured with a support mechanism, such as the patient support structure 124, to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc shaped and the support members 112 movable along the arc to position the detector units 114 at different locations along the gantry 104. In some embodiments, the detector units 114 may also be independently movable along the gantry 104.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each of the imaging detectors 102 has a radiation detection face, which is directed towards the subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or inbetween two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 110, imaging detectors 102, gantry 104 and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow coordinated move of the detector array 106 or 108. For example, the detector controller 136 may control lateral movement of the detector carriers 116 illustrated by the L arrow (and shown as left and right as viewed in FIG. 1).

The pivot controller 138 may control pivoting, rotating, or swinging movement of the detector units 114 at ends of the detector carriers 116, the detector units 114 under the patient support structure 124, and/or the detector carrier 116. For example, one or more of the detector units 114 or detector carriers 116 may be rotated or swung about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 110, gantry 104, patient table 120 and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector arrays 106 and 108, which as illustrated in FIG. 1 are in a retracted position away from the subject 110 (in the detector array 106) Positioning may be accomplished manually by the operator and/or automatically, which may include using other images acquired before the current acquisition, such as by another imaging modality such as CT, MRI, X-Ray, PET or ultrasound. Additionally, the detector units 114 may be configured to acquire non-NM data, such as x-ray CT data.

After the imaging detectors 102, gantry 104, patient table 120, and/or collimators 122 are positioned, one or more images are acquired by one or more of the imaging detectors 102 being used, which may include pivoting or swinging motion of one or more of the detector units 114, which may pivot, rotate or swing to different degrees or between different ranges of angles. The image data acquired by each imaging detector 102 may be combined and reconstructed into a composite image, which may comprise two-dimensional (2D) images, a three-dimensional (3D) volume or a 3D volume over time (4D).

In one embodiment, the imaging detectors 102, gantry 104, patient table 120, and/or collimators 122 remain stationary after being initially positioned. In another embodiment, an effective field of view for one or more of the imaging detectors may be increased by movement such as pivoting, rotating, or swinging one or more of the imaging detectors 102, rotating one or more of the detector arrays 106 and/or 108 with the gantry 110, adjusting one or more of the collimators 122, or moving the patient table 120.

In various embodiments, a data acquisition system (DAS) 160 receives electrical signal data produced by the imaging detectors 102 and converts this data into digital signals for subsequent processing. An image reconstruction device 162 and a data storage device 164 may be provided in addition to the processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images.

Additionally, a detector position controller 165 is also provided, which may be implemented in hardware, software, or a combination thereof. For example, as shown in FIG. 1, the detector position controller 165 may form part of or operate in connection with the processing unit 150. In some embodiments, the detector position controller 165 may be a module that operates to control the movement of the imaging detectors 102, including the detector units 114, such that coordinated or synchronized movement is provided as described herein. It should be noted that movement of a plurality of the imaging detectors 102 and/or detector units 114 may be performed at the same time (e.g., simultaneously or concurrently) or at different times (e.g., sequentially or step wise, such as back and forth between two detector units 114).

Figure 2:
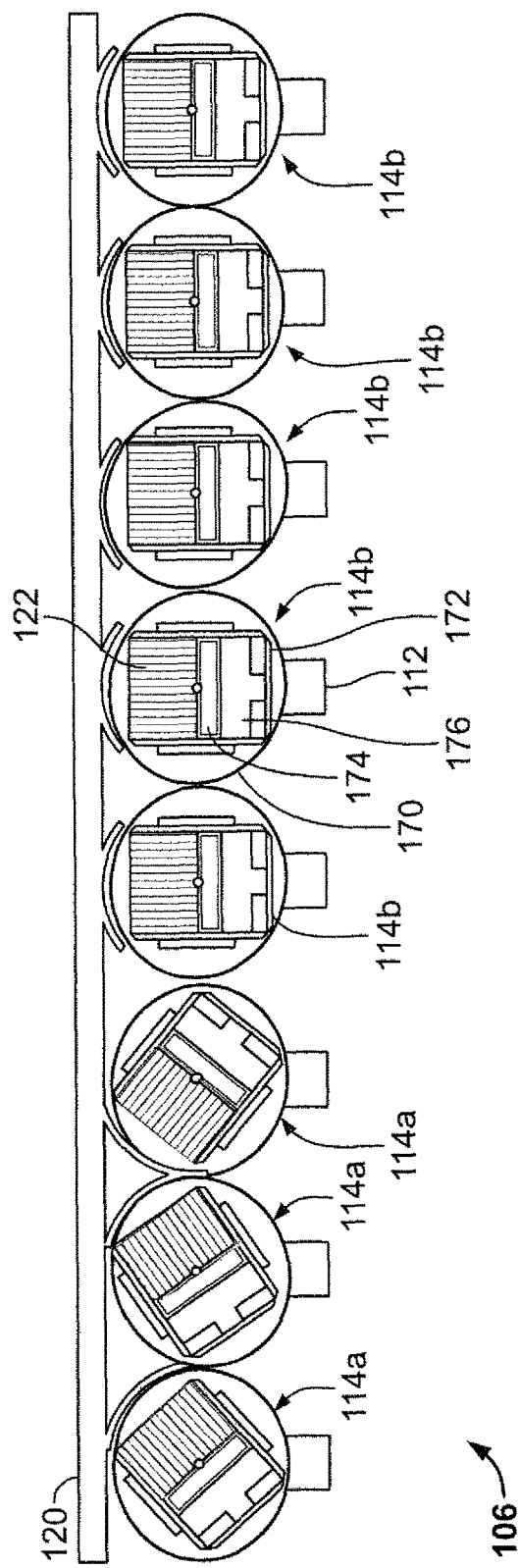
FIG. 2 is a schematic block diagram illustrating detector units in accordance with an embodiment.

In operation, and as shown, for example, in FIG. 2, one embodiment includes the detector array 106 positioned (e.g., mounted) under the patient table 120. As can be seen, a plurality of detector units 114 are positioned in adjacent arrangement, for example, along one or more rows under the patient table 120 (it should be noted that only a single row of detector units 114 is shown). The detector units 114 in some embodiments are aligned along one or more axes generally perpendicular to the longitudinal axis of the patient table 120, which defines an examination axis (e.g., from head to toe of the subject 110). However, it should be appreciated that the detector units 114 may be aligned in different configurations and orientations, which may be offset from each other, transverse to the longitudinal axis of the patient table 120 and/or parallel to the longitudinal axis of the patient table 120.

As can be seen in the illustrated embodiment, each of the detector units 114 includes a housing 170, which are illustrated as circular. However, the housing 170 of the detector units 114 may have different shapes and sizes, for example, oval, other curved shapes, etc. The detector units 114 include within the housing 170 a detector support 172, which may be a frame or other support structure. A detector 174 is coupled to the detector support 172. For example, the detector 174 may include one or more CZT tiles or modules as described herein, which are connected to electronics 176 (e.g., output electronics to output detected events) therein. Additionally, the collimator 122 is mounted to a front detecting surface of the detector 174. Thus, the detector support 172 is sized and shaped, such as having a base and/or walls, to support and maintain the components of the detector unit 114 within the housing 170. For example, the components of the detector unit 114 are maintained within the housing 170 when the housing rotates, pivots, or swings as described in more detail herein. In the illustrated embodiment, the detector units 114a are shown in a rotated, pivoted, or swung position, while the detector units 114b are shown in a non-rotated, non-pivoted, or non-swung position. As can be seen, in the non-rotated, non-pivoted, or non-swung position, the detecting face of the detector 172 is generally parallel to the patient support surface of the patient table 120, while in the rotated, pivoted, or swung position, the detecting face of the detector 172 is not parallel to the patient support surface of the patient table 120. Various embodiments provide coordinated or synchronized movement of the detector units 114, which allows the detector units 114 to be positioned or packed in closer alignment than in conventional systems. For example, in some embodiments, different detector units 114, such as adjacent detector units 114, may move along different angular ranges, to a different angular position, and/or at different velocities.

It should be noted that the arrangement of detector units 114 in the detector array 106 may be provided in other portions of the NM imaging system 100, such as at positions along the gantry 104 or as part of the detector array 106. Also, it should be noted that in some embodiments, a housing 170 is not provided surrounding or encasing the components within the detector units 114. For example, the detector units 114 may be located and housed within the patient support structure 124 (as shown in FIGS. 3 and 4), such that the patient support structure 124 provides protection from environmental elements.

As described herein, movement of the detector units 114 may be controlled to reduce or avoid collisions between the detector units 114, as well as to reduce or avoid the field of view of one or more of the detector units 114 being blocked or obstructed by one or more of the other detector units 114. For example, as shown in FIG. 3, the field of views of the detector units 114a are obstructed by an adjacent detector unit 114a (as illustrated by the O arrow). As should be appreciated, a portion or all of the field of view of the detector units 114a may be obstructed by the adjacent detector units 114a, such as depending on the angle of rotation or orientation of each of the detector units 114.

In various embodiments, the movement of one or more of the detector units 114 is controlled in relation or relative to the movement, position, and/or orientation of one or more of the other detector units 114, such as adjacent detector units 114. The controlled movement of the detector units 114 may include controlling movement, for example, of one of a pair of adjacent detector units 114 or both of a pair of adjacent detector units 114. For example, as shown in FIG. 4, the end detector unit 114a is rotated to the right as viewed in this figure. As can be seen, coordinated or synchronized movement of the detector unit 114b is also provided such that an unobstructed field of view is provided for the detector unit 114a, while avoiding contact with the adjacent detector unit 114b. In some embodiments, the coordinated or synchronized movement results in a completely unobstructed view or a reduced obstructed view as compared to not providing such movement. As should be appreciated, in various embodiments, the relative positions of each detector unit 114 with respect to one or more adjacent detector units 114 (the end detector units 114 will only have one detector unit 114 adjacent thereto) is determined. Using information for all or some of the positions and/or orientations of the detector units 114, when one or more of the detector units 114 is moved, one or more of the other detector units 114 may be moved to reduce or eliminate field of view obstructions or collisions. It should be noted that position information, such as location and/or orientation information may be stored in a database 167 (shown in FIG. 1), which may be, for example, a look up table that is updated periodically, such as after one or more of the detector units 114 is moved.

As another example, when one of the detector units 114 moves, an adjacent detector unit 114 may not need to be moved. For example, with the movement of the detector unit 114c as shown in FIG. 4, if the detector unit 114d was in the position shown, the detector unit 114d is not moved as the angle of rotation of the detector unit 114c is such that the detector unit 114d is not blocking the field of view of the detector unit 114c. Accordingly, one or more of the detector units 114 may not move. Additionally, if one or more of the detector units 114 is inactive, for example, is not going to acquire data or is not properly functioning, the detector unit 114 may be placed in a position of reduced or least likelihood of blocking the field of view of another one of the detector units 114, and then moved as needed.

In various embodiments, each of the detector units 114 includes a position sensing device, such as one or more positions sensors or encoders that are used to determine the orientation and/or angle of rotation of each of the detector units 114. It should be noted that the position sensors may also be used to determine the location or position of the detector unit 114 along other axes of movement. For example, if one or more of the detector units 114 is capable of linear movement or movement along or about other axes, the position sensors are configured to detect the location or position of the detector unit 114 as a result of any such movement. In various embodiments, one or more position sensors may be provided in connection with each of the detector units 114. Additionally, the position sensors may determine, for example, the position or orientation of the detector unit 114 to which the position sensor is attached and optionally the relative position or orientation of another detector unit 114, such as an adjacent detector unit 114. Thus, the position sensor may be configured to detect the position of the detector unit 114 along multiple axes of movement and/or rotation. For example, the position sensors may be configured to determine the position and/or orientation of the detector units 114 within a three-dimensional space, such as the X,Y,Z location of the detector units 114 within the patient support structure 124. For example, one or more of a proximity sensor (e.g., optical sensor) and/or rotary encoder (e.g., angular sensor) may be used. Accordingly, in various embodiments the position sensors may be linear, angular and/or multi-axis position sensors. Additionally, the position sensors may be absolute position sensors and/or relative position sensors (e.g., displacement sensors). In some embodiments, a Global Positioning System (GPS) arrangement may be provided. It should be noted that in some embodiments, any suitable position sensor as known in the art also may be used.

In operation, based on the determined position and/or orientation (e.g., rotated angle) of the detector units 114, and in some embodiments, using the known size of the detector units 114 or the known size of the field of view of the detectors 174, a determination may be made as to whether the field of view of one of the detector units 114 is being blocked or will be blocked by another one of the detector units 114, as well as whether a collision may occur. For example, if a determination is made that either a field of view is going to be blocked or a collision will occur if movement is continued, various embodiments may stop movement of the detector unit 114, change a direction of movement (e.g., rotating, swinging or linear movement) of the detector unit 114, or cause one or more adjacent detector units 114 to move. As should be appreciated, in various embodiments, this determination is made as to some or all of the detector units 114 within a detector array once the position or orientation of any one of the detector units 114 is changed or adjusted. Thus, when any one of the detector units 114, such as shown in FIG. 4, are moved, a determination is made as to whether any of the other detector units 114 is to be moved.

Figure 5:
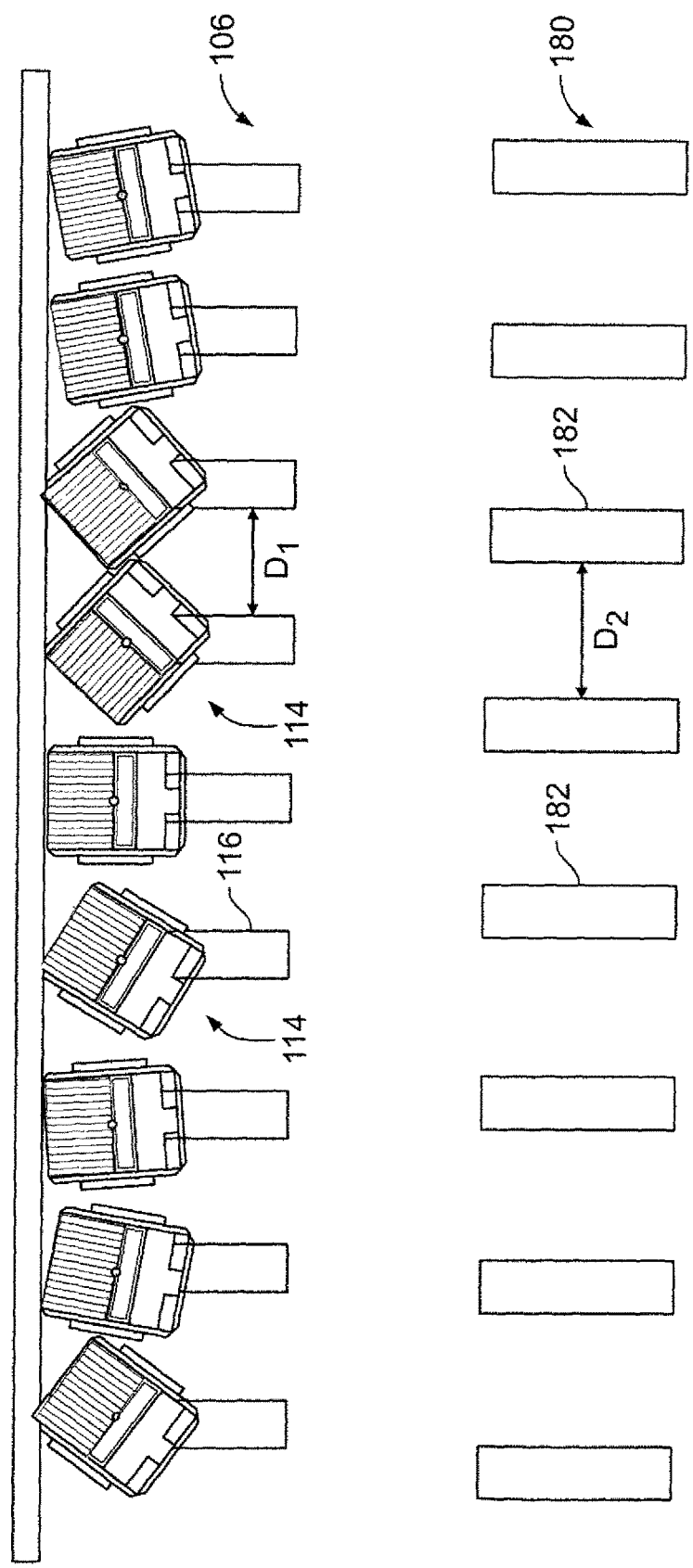
FIG. 5 is a schematic block diagram illustrating detector unit spacing.

Thus, various embodiments provide control of the movement of the detector units 114 based on a position, orientation and/or relative movement of one or more of the other detector units 114. This control in various embodiments allows the detector units 114 to be positioned closer together as a result of the field of view obstruction avoidance and collision avoidance. For example, as shown in FIG. 5, the detector units 114, and in particular the support members thereof, illustrated as the movable detector carriers 116 are spaced apart by a distance $D_1$. In particular, adjacent movable detector carriers 116 are spaced apart by the distance $D_1$. In systems without coordinated or synchronized movement, each of a plurality of support members 182 (the detector units attached thereto are not shown for ease of illustration) in a detector arrangement 180 are spaced apart from an adjacent support member 182 by a distance $D_2$. As can be seen and as should be appreciated, the distance $D_1$ is less than the distance $D_2$. The distance $D_2$ is greater to prevent collision and/or blocking of field of views of the detector units that may be moved together, but are not coordinated or synchronized as described herein as the distance is greater than the range of motion of the detector units. In some embodiments, the distance $D_1$ between support members is reduced by 10% relative to the distance $D_2$, while in other embodiments, the distance may be reduced by more, such as 15% or 20% (or more). In other embodiments, the distance between support members may be reduced less. For example, the distance $D_1$ in some embodiments is 60 cm, while the distance $D_2$ is 80 cm. However, other distances may result, such as based on the size and shape of the detector units.

In various embodiments, the detector position controller 165 is configured to control the position of the detector units 114, wherein at least some of the rotatable detector units positioned adjacent to each other have an angle of rotation configured to allow movement of the rotatable detector units a distance greater than a gap (i.e., the distance $D_1$) between adjacent detector units 114. Thus, in various embodiments, the distance between adjacent detector units 114 is such that detector units 114 are movable to an extent or angular degree greater than the distance to an adjacent detector unit 114. Accordingly, without the coordinated movement of various embodiments, adjacent detector units 114 can collide or block the field of view of each other.

Figure 6:
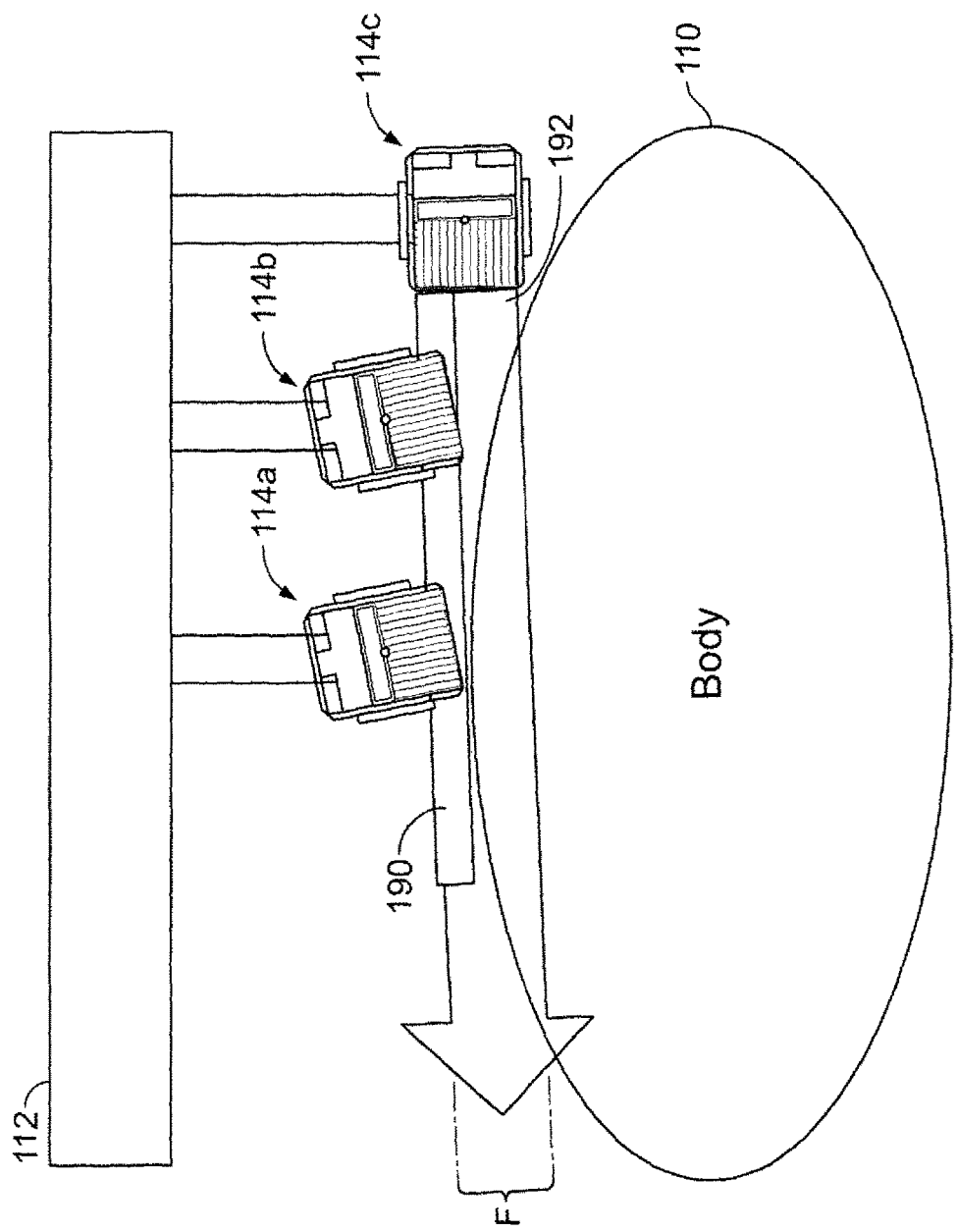
FIG. 6 is a schematic block diagram illustrating a partial field of view obstruction in accordance with an embodiment.

In some embodiments, a determination may be made as to whether and/or how much the obstructed view will affect image reconstruction. For example, as shown in FIG. 6, the field of view of the detector unit 114c is partially obstructed by the detector units 114a and 114b. In this embodiment, the detector units 114*a* and 114*b* are closer to the support member 112 than the detector unit 114*c* to provide detector units 114*a*-114*c* that are positioned proximate or adjacent to the subject 110 without contact (e.g., within a predetermined distance or range of distance). As can be seen, a portion 190 of the field of view (F) of the detector unit 114*c* is obstructed, while a portion 192 of the field of view F is not obstructed. Thus, for example in NM imaging (e.g., SPECT imaging), gamma counts emitted from the subject 110 that would otherwise impinge on and be detected by the region of the detector unit 114*c* that corresponds to the portion 190 of the field of view, are blocked and not detected. It should be noted that the obstructed portion 190 may include a region within the subject 110 or outside the subject 110.

As can be seen in FIG. 6, while the portion 190 of the field of view of the detector unit 114*c* is obstructed, the field of views of the detector units 114*a* and 114*b* encompass the obstructed portion. In particular, the detector units 114*a* and 114*b* will receive image data (e.g., photon or emission counts from within the subject 110) that otherwise would have been detected by the obstructed portion 190 of the field of view of the detector unit 114*c*. Accordingly, in some embodiments, obstructed portions of field of views of one or more of the detector units 114 may not affect or have a minimal effect on image reconstruction, such as when other detector units 114 are acquiring data in the obstructed portion. Thus, in some embodiment, when a determination is made that image data within an obstructed field of view of one or more detector units 114 is or will be acquired by one or more other detector units 114, movement of the detector unit(s) 114 may not be provided. It should be noted that in some embodiments, using coordinated or synchronized movement as described herein, the detector units 114 may be moved to increase or optimize image data acquisition, which may result in positioning one or more of the detector units 114 to have a partially obstructed field of view that is encompassed by one or more of the other detector units 114.

In some embodiments, where a field of view of one of the detector units 114 is obstructed and the field of view of none of the other detector units 114 encompasses the obstructed portion, the image reconstruction may be adjusted or modified to account for such obstruction. For example, only data acquired in the unobstructed portion of the field of view is used during image reconstruction and data in the obstructed portion (e.g., detector pixels corresponding to the obstructed field of view) are discarded. For example, in obstructed portions, the corresponding pixels of the detector may not be used, such that the zero count or reduced count image data is not used as part of the image reconstruction. Thus, in some embodiments, any data (e.g., no count data or reduced count data) from the obstructed portion of the image detector is not used.

In various embodiments, a Venn diagram or set diagram type of analysis may be performed to determined field of view obstruction(s) and/or possible detector unit collisions. For example, the field of views of the detector units 114 may be represented in one Venn diagram or set diagram type analysis and detector collision in another Venn diagram or set diagram type analysis. By determining overlapping regions in the diagrams, a determination may be made as to one or more of the detector units 114 to move, which may be based on, for example, which detector unit 114 may be moved the least or have the least effect on the other detector units 114, such as then causing one or more of the other detector units 114 to have to move. It should be noted that in some embodiments, one or more subsets of detector units 114 may be grouped together as part of the analysis.

Figure 7:
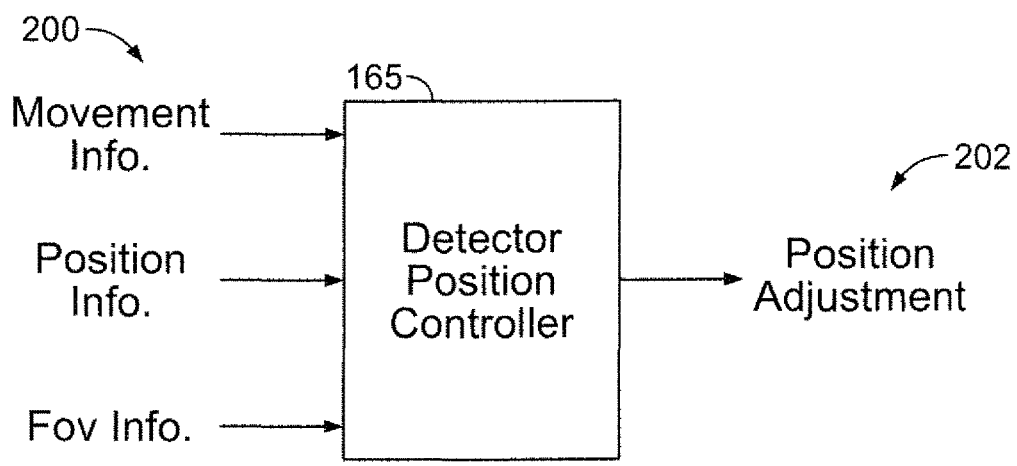
FIG. 7 is a block diagram of a detector position controller in accordance with an embodiment.

It should also be noted that the analysis may be performed, for example, by the detector position controller 165 and/or processing unit 150. For example, as illustrated in FIG. 7, the detector position controller 165 may receive as input data 200 different information for one or more of the detector units 114. In the illustrated example, the input data 200 includes movement information, such as a current movement of one of the detector units 114 that changes a position or orientation thereof. Additionally, the input data 200 may include position information for the detector unit 114 being moved, including an initial position and a final or destination position, as well as position information for one or more of the other detector units 114, such as a current position and/or orientation of adjacent detector units 114. Additionally, the input data 200 may include field of view information for the detector unit 114 that has moved or is to be moved, as well as for one or more of the other detector units 114.

The detector position controller 165 then processes the input data 200, for example, analyzes the data for field of view avoidance and collision avoidance. The detector position controller 165 then outputs one or more position adjustment signals 202 to control the movement of one or more of the detector units 114. For example, the position adjustment signals 202 may command or cause one or more of the adjacent detector units 114 to change position or orientation, which likewise then may result in additional input data 200 for those detector units 114 to be processed similarly. The position adjustment signals 202 may also command or cause the detector unit 114 that is being moved to stop movement thereof or change movement thereof, such as based on position information or field of view information of one or more of the other detector units 114 that also may be moving. For example, overlaps in the locations of the detector units 114, which may be indicative of possible collision or field of view obstruction, may be determined.

It should be noted that the input data may be obtained, for example, form the database 167 (shown in FIG. 1). Additionally, the data in the database 167 may be updated based on the position adjustment signals 202, such as to update the location or orientation of one or more of the detector units 114.

Figure 8:
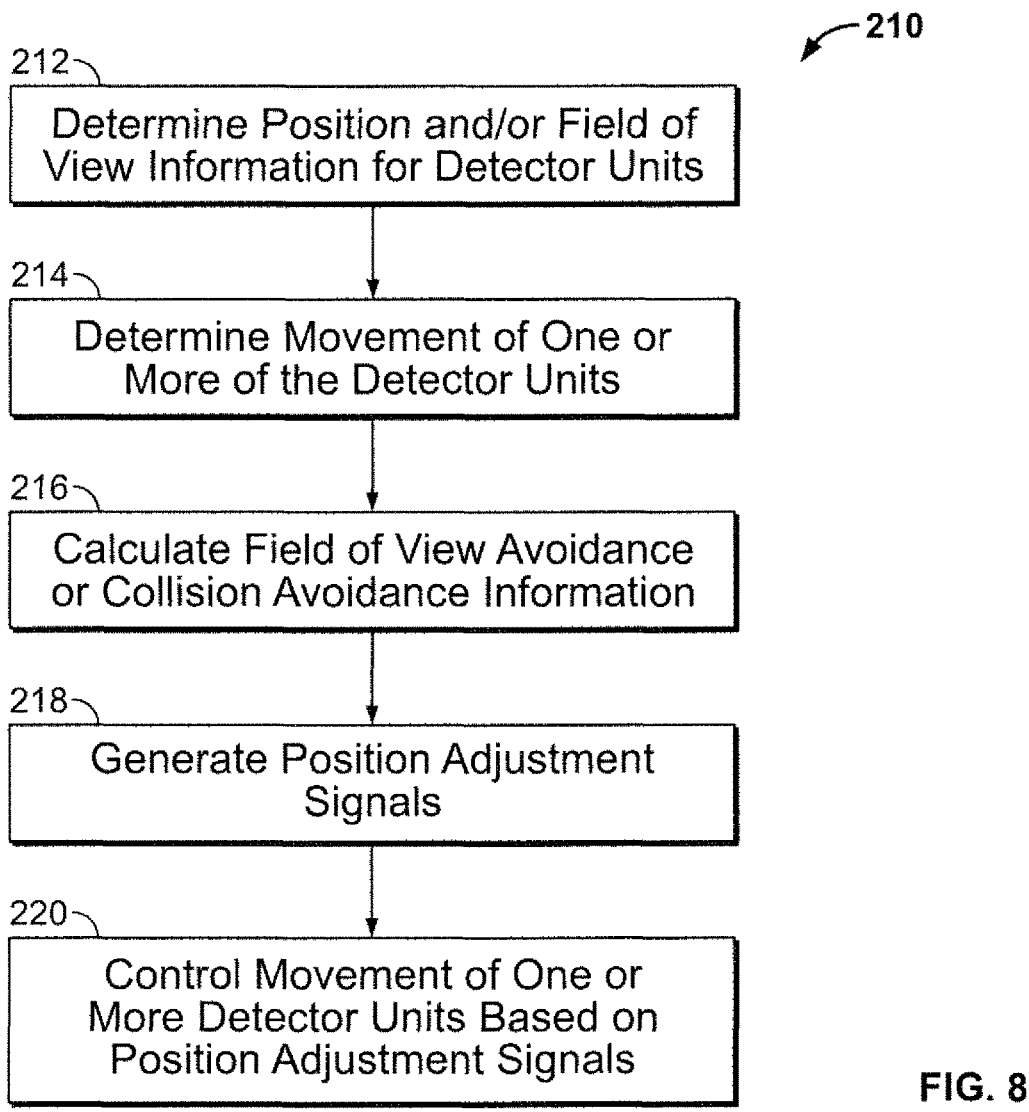
FIG. 8 is a flowchart of a method for controlling movement of detector units in accordance with various embodiments.

In some embodiments, the detector position controller 165 may implement one or more methods or algorithms, such as the method 210 shown in FIG. 8. In various embodiments, the method 210, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

In particular, the method 210 includes determining at 212 position and/or field of view information for a plurality of detector units, such as the detector units 114. For example, the absolute or relative positions and orientations of a plurality of detector units, as well as defined field of views (e.g., based on known characteristics, such as size and shape of the detector) may be accessed from a stored database. The stored information may include position and/or field of view information as updated based on any previous movements of one or more of the detector units.

The method 210 also includes determining movement (e.g., rotation or swinging) of one or more of the detector units at 214. For example, one or more of the detector units may be moved, such as repositioned. Using one or more position sensors as described herein, the movement, such as the movement destination, of the detector unit(s) may be determined. Thus, for example, an initial position of the detector unit(s) and a destination position of the detector unit(s) may be determined. This determination may also include information relating to a proposed movement of the detector unit(s), such as based on one or more inputs, such as user inputs or imaging protocol steps.

The method 210 further includes calculating field of view avoidance or collision avoidance information at 216. For example, based on the determined movement at 214 and the known current locations and positions of the plurality of detector units, including the field of views of each detector unit (it should be noted that some of the detector units may have different fields of views than other detector units), avoidance information may be calculated as described herein. For example, the calculated avoidance information may determine any obstructed fields of views or collisions resulting from the determined movement at 214. It should be noted that the calculation of the avoidance information may include an iterative or multi-step process, particularly when more than one detector unit is moving, such as when an adjacent detector is also moved as a result of the movement of one of the detector units. In some embodiments, for example, a geometric analysis or modeling may be performed to determine new positions or orientations for one or more adjacent detector units relative to the moving detector unit. However, it should be appreciated that other methods as described herein (or otherwise) may be used to control or optimize the coordinated or synchronized movements of the detector units, which may include reducing or eliminating field of view obstructions or detector unit collisions. The calculations at 216 may include, for example, processing a plurality of different combinations of possible movements of the detector unit(s) to determine one movement or sets of movements that reduces or eliminates field of view obstructions or detector unit collisions.

Using the calculated avoidance information, position adjustment signals are generated at 218. For example, one or more signals may be generated for communication to one or more of the detector units. The signals may command or cause the one or more detector units to move to a new position or orientation. In particular, the movement of one or more of the detector units is controlled at 220 based on the position adjustment signals. In various embodiments, movement of a plurality of the detector units is coordinated or synchronized based on the calculated avoidance information. The movements may occur at the same time or at different times. For example, one or more than one of the detector units may move simultaneously or concurrently.

Thus, various embodiments provide coordinated control of the movement of a plurality of detector heads. The movements in various embodiments provide field of view obstruction avoidance and/or collision avoidance. Accordingly, the spacing of the detector unit may be reduced and without the various embodiments, collisions or obstructed fields of view may result.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
    a plurality of detector units configured to be coupled to at least one of a gantry or a patient support structure, at least some of the detector units being at least one of rotatable or translatable to position the detector units at different angles relative to a patient; and
    a detector position controller configured to control the position of the detector units, at least some of the detector units positioned adjacent to each other, the detector position controller further configured to calculate field of view avoidance information to determine an amount of movement for a proposed movement from an initial position to a destination position for one or more of the detector units, wherein the field of view avoidance information corresponds to obstructions in a field of view of at least one of the detector units for the proposed movement, wherein the detector position controller is configured to determine whether or not image data within an obstructed field of view of one or more of the detector units will be acquired by one or more others of the detector units.

2. The imaging system of claim 1, wherein the detector position controller is further configured to rotate the at least one of the detector units to at least one of avoid or reduce field of view obstruction of adjacent detector units.

3. The imaging system of claim 1, wherein the detector position controller is further configured to translate the at least one of the detector units away from the patient to at least one of avoid or reduce field, of view obstruction of adjacent detector units.

4. The imaging system of claim 3, wherein the detector position controller is further configured to linearly translate the at least one of the detector units away from the patient.

5. The imaging system of claim 4, wherein the detector position controller is further configured to translate the at least one of the detector units radially to at least one of avoid or reduce field of view obstruction of adjacent detector units.

6. The imaging system of claim 3, wherein the detector position controller is further configured to translate the at least one of the detector units away from an adjacent detector unit to at least one of avoid or reduce field of view obstruction of adjacent detector units.

7. The imaging system of claim 1, wherein the detector position controller is configured to not move the one or more detector units having an obstructed field of view when it is determined that the image data within an obstructed field of view will be acquired by one or more others of the detector units.

8. The imaging system of claim 1, wherein the detector position controller is configured to move at least some of the detector units at the same time.

9. The imaging system of claim 1, wherein the detector position controller is configured to move at least some of the detector units at a different time than at least some others of the detector units.

10. The imaging system of claim 1, wherein the detector position controller is configured to calculate the field of view avoidance information using position information stored in a database, and to update the database after movement of at least one of the detectors.

11. The imaging system of claim 1, wherein the detector position controller is further configured to perform coordinated movement of a plurality of the rotatable detector units to avoid field of view obstruction of adjacent rotatable detector units.

12. The imaging system of claim 1, wherein, when at least one of the rotatable detector units has a portion of a field of view obstructed by an adjacent rotatable detector unit, the detector position controller is further configured to discard image data for the portion of the field of view that is obstructed.

13. The imaging system of claim 1, wherein the detector position controller is further configured to control movement of at least some of the rotatable detector units through a range of motion or at a different velocity than at least some of different ones of the rotatable detector units.

14. An imaging system comprising:
    a gantry;
    a patient support structure supporting a patient table thereon;
    a plurality of detector units configured to be coupled to at least one of the gantry or the patient support structure, at least some of the detector units being at least one of rotatable or translatable to position the detector units at different angles relative to a patient; and
    a detector position controller configured to control the position of the detector units, at least some of the detector units positioned adjacent to each other, the detector position controller further configured to calculate field of view avoidance information to determine an amount of movement for a proposed movement from an initial position to a destination position for one or more of the detector units, wherein the field of view avoidance information corresponds to obstructions in a field of view of at least one of the detector units for the proposed movement, wherein the detector position controller is configured to determine whether or not image data within an obstructed field of view of one or more of the detector units will be acquired by one or more others of the detector units.

15. The imaging system of claim 14, wherein the detector position controller is further configured to rotate the at least one of the detector units to at least one of avoid or reduce field of view obstruction of adjacent detector units.

16. A method comprising
    determining position and field of view information for a plurality of detector units;
    determining a proposed movement of at least one of the detector units from an initial position to a destination position;
    calculating, with the at least one of the detector units at the initial position, field of view avoidance information based on the proposed movement and current positions of at least some of the detector units, wherein the field of view avoidance information corresponds to obstructions in a field of view of the at least one of the detector units for the proposed movement;

determining whether or not image data within an obstructed field of view of one or more of the detector units will be acquired by one or more others of the detector units;

generating one or more position adjustment signals based on the calculated field of view avoidance information; and controlling movement of the plurality of detector units using the one or more position adjustment signals.

17. The method of claim 16, wherein controlling movement of the plurality of detector units comprises controlling coordinated movement of at least some of the detector units to avoid field of view obstruction.

18. The method of claim 16, further comprising not moving the one or more detector units having an obstructed field of view when it is determined that the image data within an obstructed field of view will be acquired by one or more others of the detector units.

* * * * *